United States Patent [19]

Griffiths

[11] Patent Number: 4,921,485
[45] Date of Patent: May 1, 1990

[54] CATHETER FOR USE IN THE SURGICAL CORRECTION OF A NASOLACRIMAL DUCT OBSTRUCTION

[76] Inventor: John D. Griffiths, 1738 S. 85th St., Omaha, Nebr. 68124

[21] Appl. No.: 250,164

[22] Filed: Sep. 28, 1988

[51] Int. Cl.⁵ ............................................. A61M 25/00
[52] U.S. Cl. .................... 604/104; 604/280; 606/191
[58] Field of Search ............... 604/93, 264, 280, 266, 604/268, 49, 104; 128/344; 606/191, 196, 198

[56] References Cited

U.S. PATENT DOCUMENTS

| | | | |
|---|---|---|---|
| 3,726,284 | 4/1973 | Parker | 604/104 |
| 4,490,138 | 12/1984 | Lipsky et al. | 604/264 |
| 4,500,313 | 2/1985 | Young | 604/280 |
| 4,680,029 | 7/1987 | Ranford et al. | 604/280 |

*Primary Examiner*—Stephen C. Pellegrino
*Attorney, Agent, or Firm*—Zarley, McKee, Thomte, Voorhees & Sease

[57] ABSTRACT

A catheter for use in the surgical correction of a nasolacrimal duct obstruction comprising elongated tubular portion having an enlarged mushroom-shaped head portion at the upper end thereof. When the catheter is properly placed during the surgical procedure, the head portion of the catheter prevents longitudinal displacement thereof and prevents the "scarring over" of the nasolacrimal duct.

6 Claims, 1 Drawing Sheet

CATHETER FOR USE IN THE SURGICAL CORRECTION OF A NASOLACRIMAL DUCT OBSTRUCTION

BACKGROUND OF THE INVENTION

This invention relates to a catheter and more particularly to a catheter which is used to improve the success of surgically correcting a nasolacrimal duct obstruction.

It is frequently necessary to correct, by way of surgery, a nasolacrimal duct obstruction. One method of correcting a nasolacrimal duct obstruction is through the silastic intubation of the nasolacrimal duct. In such a procedure, the free ends of a silastic tube are inserted downwardly into, and through, the puncta, canaliculi, nasolacrimal sac and nasolacrimal duct with the lower ends of the silastic tubing being positioned within the nose (inferior meatus) below the lower end of the nasolacrimal duct. The ends of the silastic tubing are normally cut so they do not protrude below the lower end of the patient's nose. The purpose of the silastic tubing is to provide a flow path for the tears to drain downwardly through the system around the exterior surface of the tubing.

One method of fixation of the silastic tubing is through the use of a rubber catheter which embraces the silastic tubing from the nasolacrimal sac to the lower end of the nasolacrimal duct. Knots or sutures are then employed to prevent upward displacement of the silastic tubing with respect to the cuff and to prevent downward displacement of the cuff with respect to the tubing.

Although fixation of the silastic tubing in the nasolacrimal system is a problem, the most troublesome problem is that scar tissue forms around the tubing thereby resulting in an obstruction which prevents tears from passing downwardly through the system around the exterior of the tubing.

It is therefore a principal object of the invention to provide a catheter for use with silastic tubing used in correcting nasolacrimal duct obstructions.

Yet another object of the invention is to provide a method of correcting nasolacrimal duct obstructions through the use of a catheter having an enlarged mushroom-shaped head portion on the upper end thereof.

Yet another object of the invention is to provide a catheter for use in the procedure described including an enlarged head portion which prevents longitudinal displacement of the catheter and the silastic tubing extending therethrough which can be left in vitro for two to six months without significant discomfort.

Still another object of the invention is to provide a catheter for use in the described surgical procedure including an enlarged head portion at the upper end thereof which may be easily compressed to facilitate the postoperative removal thereof.

Yet another object of the invention is to provide a device of the type described which includes an enlarged head portion thereon to reduce the "scarring over" of the entrance to the nasolacrimal opening into the nose.

These and other objects of the invention will be apparent to those skilled in the art.

SUMMARY OF THE INVENTION

A catheter is described for use with flexible silastic tubing having the ends thereof extended downwardly through the puncta, canaliculi, nasolacrimal sac and surgical bony opening onto the nose of a person's nasolacrimal system. The catheter has an internal diameter sufficient such that the free ends of the silastic tubing may be extended downwardly therethrough. The catheter has an enlarged head portion provided thereon at its upper end which is positioned in the nasolacrimal sac to prevent longitudinal displacement of the catheter as well as the silastic tubing. The mushroom-shaped head portion of the catheter is provided with openings formed therein to permit the insertion of the free ends of the silastic tubing therethrough. The flexible characteristics of the enlarged head portion of the catheter permits the catheter to be easily removed postoperatively without excessive trauma. The method of using the catheter is also described.

DESCRIPTION OF THE PREFERRED EMBODIMENT

Figure 4:
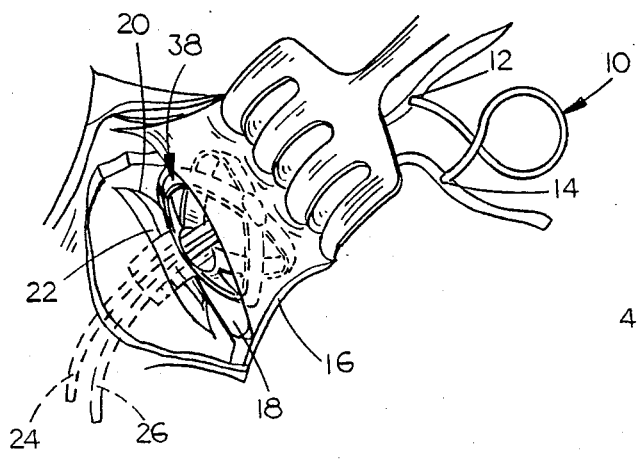
FIG. 4 is a perspective view illustrating the manner in which silastic tubing is extended downwardly through the puncta, canaliculi, into the nasolacrimal sac and outwardly through an incision created during a DCR procedure.
Figure 5:
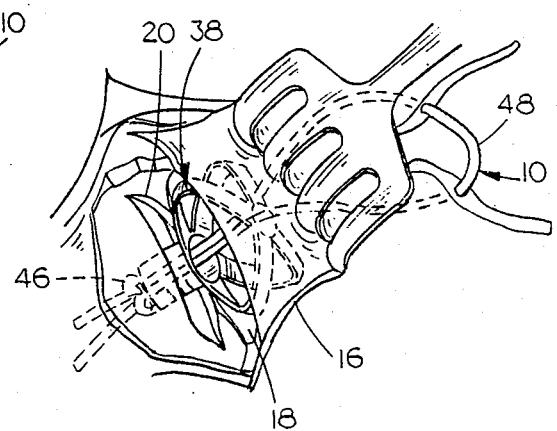
FIG. 5 is a view similar to FIG. 4 except that the catheter of this invention has been positioned in the nasolacrimal sac and the nasal cavity.

Referring to FIGS. 4 and 5, the numeral 10 refers to silastic tubing, the free ends of which are inserted downwardly through punctums 12 and 14 into the canaliculi communicating therewith. A conventional dacryocystorhinostomy procedure or technique (DCR) is performed by creating an incision 16 which communicates with the nasolacrimal sac 18. An incision 20 is also created to expose the nasal cavity 22. During the initial intubation procedure, the free ends 24 and 26 of the silastic tubing 10 are pulled outwardly through the incision 16 as seen in FIG. 4.

The numeral 30 refers to the catheter of this invention which is preferably comprised of an inert material such as silastic or some similar alloplastic material such as "C-Flex". For purposes of description, catheter 30 will be described as having an upper end 32 and a lower end 34. Preferably, the catheter 30 is provided with markings or indicia 36 provided thereon to aid the surgeon in determining the length to which the catheter should be cut. The numeral 38 refers to an enlarged mushroom-shaped head portion provided on the upper end of the catheter 30 comprised of flat, V-shaped legs 40 joined at their upper ends to form a juncture 42. For purposes of description, the numeral 44 will be used to indicate the openings between the arms 40.

Figure 1:
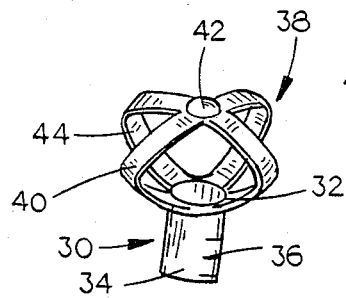
FIG. 1 is a perspective view of one form of the invention.
Figure 2:
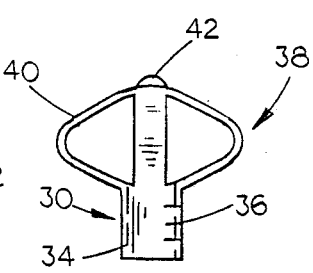
FIG. 2 is a side elevational view of the catheter of FIG. 1.
Figure 3:
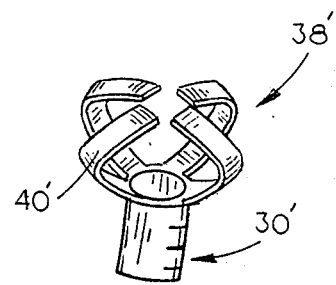
FIG. 3 is a perspective view of a modified form of the catheter.

FIG. 3 illustrates a modified form of the catheter which is referred to generally by the reference numeral 30'. Catheter 30' similarly has a plurality of flat, V-shaped arms 40' provided thereon although the upper ends of the arms 40' are not joined together as in catheter 30.

When the silastic tubing 10 has been positioned as previously described and as illustrated in FIG. 4, catheter 30 is slipped onto the free ends 24 and 26 of tubing 10 so that the ends 24 and 26 pass through a pair of the openings 44 and downwardly through the inside diameter of the catheter 30. The silastic tubing and the catheter 30 are then extended downwardly through the nasolacrimal duct as illustrated in FIG. 5 with a plurality of knots preferably being formed in the tubing 10 below the lower end of the catheter 30 to prevent upward displacement of the tubing 10 with respect to the catheter 30 and to aid in preventing the downward displacement of the catheter 30 with respect to the tubing 10. As seen in FIG. 5, when the catheter 30 is in position, the enlarged head portion 38 thereof is positioned in the nasolacrimal sac 18 and occupies a large portion thereof. The enlarged head portion 38 prevents the catheter and the silastic tubing from being pulled upwardly into the canaliculi should the patient grasp the loop generally referred to by the reference numeral 48.

The catheter 30 not only aids in fixing the silastic tubing but it also aids in maintaining a flow path for the tears through the nasolacrimal duct. The enlarged head portion of the catheter prevents the "scarring over" of the upper end of the nasolacrimal duct thereby preventing an obstruction being formed which would interfere with the flow of tears.

After the catheter has been positioned as illustrated in FIG. 5, the DCR procedure would be completed with the incision then being enclosed. After a prescribed length of time, the silastic tubing 10 would be removed. The silastic tubing 10 is removed through the use of standard procedures with the loop 48 first being cut. The flexible enlarged head portion 38 of the catheter 30 will easily compress to permit the catheter to be pulled downwardly through the nasolacrimal duct when it is desired to remove the silastic tubing 10.

It is important to note that the enlarged head portion of the catheter also permits the tubular portion of the catheter to be quite short so that it will not objectionably protrude into the patient's nostril.

Thus it can be seen that the invention accomplishes at least all of its stated objectives.

I claim:

1. In combination,
   a flexible tube having ends for extending downwardly, through the puncta, canaliculi, nasolacrimal sac and nasal cavity of a person's nasolacrimal system,
   a catheter having upper and lower ends,
   the inside diameter of said catheter being such that the free ends of the flexible tube may be extended therethrough,
   the length of said catheter being such that said catheter may be extended into the upper end of the nasal cavity with the upper end thereof positioned in the nasolacrimal sac,
   said catheter having a flexible, enlarged head portion provided on its upper end for positioning in the nasolacrimal sac.

2. The combination of claim 1 wherein said head portion comprises a plurality of spaced-apart, V-shaped fingers.

3. The combination of claim 1 wherein said head portion is mushroom shaped and has a plurality of spaced-apart openings formed therein to permit the flexible tube to be extended therethrough.

4. The method of intubating the nasolacrimal system of a patient comprising the steps of:
   performing a dacryocystorhinostomy including creation of an incision which exposes the nasolacrimal sac,
   looping the free ends of a flexible tube downwardly through the puncta, canaliculi into the nasolacrimal sac and outwardly through the incision,,
   providing a catheter having an enlarged head portion at its upper end,
   extending the free ends of the tube downwardly through the enlarged head portion of a catheter and through the catheter,
   extending the free ends of the tube and the lower end of the catheter into the nasal cavity while maintaining the enlarged head portion of the catheter in the nasolacrimal sac,
   and closing the incision.

5. The method of claim 7 wherein knots are formed in the free ends of the tube below the lower end of the catheter to prevent upward movement of the tube relative to said catheter and to aid in preventing downward movement of the catheter relative to the tube.

6. The method of claim 4 wherein the tube is secured against movement relative to the catheter.

* * * * *